(12) United States Patent  
Karapetyan

(10) Patent No.: US 7,083,412 B1  
(45) Date of Patent: Aug. 1, 2006

(54) DENTAL TOOTH SPACER ASSEMBLY

(76) Inventor: Armen Karapetyan, 1935 N. Van Ness Ave., Los Angeles, CA (US) 90068

( * ) Notice: Subject to any disclaimer, the term of this patent is extended or adjusted under 35 U.S.C. 154(b) by 0 days.

(21) Appl. No.: 11/079,826

(22) Filed: Mar. 14, 2005

(51) Int. Cl.
*A61G 7/00* (2006.01)

(52) U.S. Cl. .................................................. 433/148

(58) Field of Classification Search ............... 433/148, 433/149, 155, 39, 40
See application file for complete search history.

(56) References Cited

U.S. PATENT DOCUMENTS

| 351,065 | A | * | 10/1886 | Miller | 433/39 |
| 552,697 | A | * | 1/1896 | Peterson | 433/39 |
| 1,133,379 | A | * | 3/1915 | Hollingsworth | 433/39 |
| 5,425,635 | A | | 6/1995 | Croll | |
| 5,505,618 | A | | 4/1996 | Summer | |
| 6,736,639 | B1 | | 5/2004 | Summer | |
| 6,749,429 | B1 | | 6/2004 | Haraden et al. | |

* cited by examiner

*Primary Examiner*—Cary E. O'Connor

(57) ABSTRACT

An improved dental tooth spacer assembly provides a safe separation of the restoring tooth and the adjacent tooth during dental procedures. The improved dental tooth spacer assembly includes a separating portion made of a durable flexible material, and comprising a first wall and a second wall. Also the improved dental tooth spacer assembly includes a fixing member comprising an elongated body, a first wing and a second wing.

3 Claims, 4 Drawing Sheets

DENTAL TOOTH SPACER ASSEMBLY

FIELD OF THE INVENTION

This invention relates to a tooth spacer for use in the a dentistry and, more particularly, to separate the teeth to provide a dental work, for example, such as applying cavity filling material to a tooth.

BACKGROUND OF THE INVENTION

Presently, the tooth spacers (a.k.a. matrix bands) are a common tool used in dentistry. Matrix bands are used in dental practice to separate (isolate) restoring tooth having a proximal surface requiring restoration and an, intact proximal tooth not requiring restoration. In dentistry, teeth which are subject to decay are typically drilled or otherwise prepared by removing the decayed tooth material. This leaves an aperture, slot or other void in the tooth which is then filled with composite resin or other filling material. A Class 2 filling is a dental procedure in which a decayed area of a tooth along a portion of one or both proximal surfaces is prepared and filled. The proximal surfaces of a tooth are those surfaces of the tooth that face the surface of an adjacent tooth. The proximal surface that faces an adjacent tooth toward the front of the dental arch may be referred to as the mesial proximal surface. The proximal surface that faces an adjacent tooth toward the back of the dental arch may be referred to as the distal proximal surface.

When dentists perform Class 2 cavity preparations, they typically insert a temporary substrate adjacent to the cavity preparation to contain and shape the filling material. The temporary substrate that dentists have traditionally used is an elongated band called a matrix band. Mostly, the matrix band is of metallic material and is positioned around a tooth to be filled. The band is then tightened around the tooth, with a some kind of a clamping device, in order to form a mold or an appropriate support for applying a filling material to the tooth.

The matrix bands are a common and long-used dental implements and the problems do exist with the currently used technology. Also, the matrix bands of the most prior art are metallic.

For example, the matrix band by U.S. Pat. No. 6,749,429 a support base with a coating, at least one aperture (preferably two apertures may be centrally located in the width area of coated matrix band) used to assist in the removal of coated matrix band by a dental instrument, e.g. such as an explorer. More particularly, the matrix band comprises a stainless steel support base, the coating being based on either a tin alloy of 2 percent by weight gold and 98 percent by weight tin, being applied to a tooth under repair, or the tin alloy is replaced with an alloy of 2 percent by weight tin and 98 percent by weight indium, or the tin alloy is replaced with an alloy mixture of equal parts by weight of 2 percent by weight gold and 98 percent by weight tin and two percent by weight tin and 98 percent by weight indium.

Two diametrically opposed apertures are preferably presented in the matrix band of the diameter providing the explorer, fits in apertures and facilitates removal of the matrix band.

While these known matrix bands provide their functional purpose, they are complex considering the presence of the apertures and necessity to use additionally the dental instrument, e.g. such as explorer. Additionally, such matrix bands (surrounding the tooth) do not provide access to the cavity located in the lowest part of the outside portion of the tooth, and the sharp lowest edge can injure the gingiva (if spacer stays not exactly vertically /under the angle to the horizontal level/ or gum (if spacer stays exactly vertically to the horizontal level).

It is known, that before being placed in the patient's mouth, a matrix band usually is placed in a retaining device or other type of tool to position and tighten the band around the tooth so that it at least partially surrounds and conforms closely to the shape of the tooth.

When restoring a tooth, it is known and important to achieve a closed contact between the restored surface and the adjacent tooth to prevent food from becoming impacted between the teeth and causing periodontal disease. One problem with conventional matrix bands is that when they are removed from a Class 2 filling made with composite filling material, a gap often remains between the filled tooth and the adjacent tooth. The gap is typically roughly as wide as the thickness of the matrix band which was used in the filling. In order to solve the problem of open contacts in Class 2 composite fillings, dentists sometimes employ special techniques and tools to separate or otherwise force apart the adjacent teeth during the filling process. After the filling material is cured, the device separating the adjacent teeth is removed to permit the teeth to spring back together, hopefully just far enough to leave a fully closed contact between the teeth. One specific technique involves the use of mechanical separation driven in place by finger pressure between adjacent teeth at a location well below the contact area. Another known technique involves forcefully separating the teeth by use of a metal ring which applies powerful forces inward between the teeth at a location just beneath where they meet.

Sometimes, such forceful separation of adjacent teeth may be difficult for the dentist and uncomfortable for the patient. Another disadvantage of using techniques involving forceful separation of adjacent teeth is that the extent to which the teeth will spring back together following the procedure is somewhat unpredictable. Moreover, in a Class 2 filling in which a matrix band is positioned around a tooth having a prepared proximal surface (i.e., a proximal surface requiring restoration) and an intact proximal surface (i.e., a proximal surface not requiring restoration), the thickness of the band between the intact proximal surface and an adjacent tooth tends to push, or drive, the tooth being filled toward the tooth adjacent the prepared surface. Consequently, additional force is required to adequately separate apart the adjacent teeth on the side of the prepared surface for packing the filling material into the cavity.

As well known in the dental practice, the attempts to solve the problem of open contacts that requires less forceful separation of adjacent teeth are to use matrix bands having areas of reduced thickness for insertion between the proximal surfaces of adjacent teeth. However, if a tooth has only one prepared proximal surface, matrix bands of this type can be difficult to place between the tight intact interproximal contact (i.e., the contact between the intact proximal surface not requiring restoration and an adjacent tooth) because the band is very thin and pliable. Such a band may buckle or tear and may not slide through the intact interproximal contact. Shorter matrix bands provide a form to enclose the proximal surface requiring restoration but are not long enough to completely encircle the tooth, and therefore do not require insertion between the intact interproximal contact. One popular version of a shorter band is known as a sectional matrix. However, such short matrix bands are undesirable in that they are difficult to tighten around a tooth and maintain a close contact between the inner surface of the band and the outer contour of the prepared tooth to avoid the formation of a ledge at the gingival edge of the filling.

Therefore, the dental insert (matrix band) by U.S. Pat. No. 6,736,639 is represented by an elongated band having first and second spaced apart central portions. According to this aspect of the disclosure, a tooth insert is provided for engaging around a first tooth having a prepared proximal surface requiring restoration adjacent to a second tooth and an intact proximal surface adjacent to a third tooth at the opposite side of the first tooth from the second tooth. The described in this invention matrix band comprises a gingival edge and an occlusal edge which is opposed to and spaced from the gingival side, a pair of opposite transversely spaced side edges extending between the respective gingival and occlusal edges. The "gingival edge" refers to the edge of the body which is positioned closest to the patients gum when the band is inserted in place. Also the band comprises an elongated body having first and second elongated leg portions that join together at a central region. The body is of the inverted v-shaped configuration with the apex of the configuration being positioned at the central region, and has two spaced apart central portions, each of which is positioned in a respective one of the elongated leg portions. The central portions are desirably located on the body so that they are positioned at least in part proximal surfaces of adjacent teeth. Thus, the first central portion is positioned between the adjacent surfaces of teeth and while the another central portion is positioned between the adjacent surfaces of teeth.

The restoring tooth is located on the mesial side of tooth, and the adjacent tooth is located on the distal side of tooth. The restoring tooth has a prepared cavity on its distal proximal surface. The mesial proximal surface of tooth is intact and does not require restoration. The adjacent teeth have interproximal contact areas where the teeth are closest to or in contact with one another. Thus, a distal interproximal contact is formed between the distal proximal surface of tooth and the mesial proximal surface of the adjacent tooth. The cavity preparation has completely eliminated the interproximal contact between teeth. A mesial interproximal contact is formed between the mesial proximal surface of the restoring tooth and the distal proximal surface of it. The leg portion of the band contains a centrally located aperture positioned in central portion to permit at least partial interproximal contact between the intact proximal surface of teeth: The aperture minimizes separation of teeth. Aperture is oval in shape, with the major axis of the aperture extending generally lengthwise of the band, and is dimensioned to be larger than the area occupied by the intact interproximal contact, such as larger than the contact area of the teeth to maintain the full interproximal contact therebetween and to eliminate separation caused by the thickness of the band when the band is positioned around a tooth.

When the band is in place around a tooth for filling, the band does not cause that tooth to move toward a tooth adjacent to the prepared cavity. As a result, additional separation of the restoring tooth with the prepared proximal surface and an adjacent tooth is not required to result in an acceptably tight finished interproximal contact. The aperture must not be so large as to overly weaken leg portion. Leg portion is rigid to withstand the pressure needed to push it down through the intact interproximal contact without tearing or buckling. The aperture is spaced from the gingival edge and the occlusal edge of leg portion so that a peripheral or reinforcing region of the body bounds aperture. Such a construction enhances the rigidity of leg portion 6 to facilitate the insertion of leg down through the intact interproximal without the leg 6 tearing or buckling. The outline of the body may be extended in the occlusal direction to form a projection (lip) over the aperture. The projection adds rigidity to leg portion around aperture and also provides a convenient location on which a dentist can apply finger pressure in order to push the gingival edge of leg portion down through the intact interproximal contact area between teeth.

This matrix band has the same deficiencies, i.e. it is complex considering the presence of the apertures, and such matrix bands (surrounding the tooth) do not provide convenient access to the cavity located in the lowest part of the outside portion of the restoring tooth. Additionally, the sharp lowest edge can injure the gingiva (if spacer stays not exactly vertically /under the angle to the horizontal level/) or gum (if spacer stays exactly vertically to the horizontal level).

As have been described above the matrix bands are commonly used to confine the placement of a Class 2 dental restoration and to provide anatomical form to the restoration for proper proximal contact of posterior teeth, and, as have been mentioned, the matrix bands traditionally completely encircle the tooth and remain stable and inflexible during placement of the restorative material, providing the restoration with a smooth surface and assuring that properly condensed or injected restorative material will not escape the confines of the band, causing excess at cavosurface margins. A screw-tightened, mechanically-retained matrix band system is widely used. The problem with custom-contoured matrix bands is that they require a great deal of operating time. The use of individual matrix segments hand-cut from a long strip of suitable material which are then custom-shaped by the dentist during the restoration procedure is known, however, this process is also time-consuming and achieving intricate shapes of the matrix strips is not possible using dental hand cutting tools.

Therefore, the matrix band segment by U.S. Pat. No. 5,425,635 is a portion of matrix material sufficient to cover the interproximal area of the restoration which is shaped for easy application and removal. According to the procedure disclosed herein, the matrix segment is shaped to the tooth contour, applied interproximally between the teeth. The segment is then can be removed in the occlusal direction. Occlusal matrix removal can fracture setting amalgam. Application and removal of the segment is accomplished by use of pliers; or optionally, the segment may be removed by means of attaching and pulling it away with a string-like material such as dental floss or thicker dental tape.

The matrix band segment comprises a top and a bottom portions with opposing left and right sides. The top portion is wider than the bottom portion, and to prevent laceration of the gingival tissues, the sides have smooth tapered edges. The sides converge in the direction of the bottom portion. The top portion includes plier-gripping ears that facilitate the placement and removal of the segment. One or both of the ears may include an aperture for the optional application of a removal string. The segment is first contoured with contouring pliers well-known in the dental arts to replicate the original proximal anatomical form. The contoured segment is applied between teeth and slightly bent around the restoring tooth. The matrix segment is now in place for the application and condensation of restorative material. The matrix segment is then removed. To assist in removing the string is applied through an aperture in one ear of the segment, and the segment laterally removed by pulling the string. The string also serves as a safety tether, preventing the segment from inadvertent displacement during the dental procedure.

This matrix band is complex considering the presence of the apertures and the string, preventing the segment from inadvertent displacement during the dental procedure. Also, the sharp lowest edge can injure the gingiva (if spacer stays not exactly vertically /under the angle to the horizontal level/ or gum (if spacer stays exactly vertically to the horizontal level).

Usually, the known conventional matrix bands have been at least ten microns in thickness and separate the teeth apart slightly. This separation has not been a problem when used with amalgam filling material packed between two adjacent teeth. However, new aesthetically pleasing and structurally strong materials have been developed such as composite resin materials. The new composite resin materials is that they cannot be packed as easily into a tooth cavity as amalgam. Also, the thick tooth spacers (matrix bands, strips, etc.) have been used to accomplish this desired separation. As a result, following filling and when the strips are removed, a small space or gap is left between the teeth. Any such gap or interproximal space, even when very small, is a trap for food to lodge between the teeth during chewing. This as was mentioned above contributes to tooth cavities and gum diseases, such as periodontal disease.

Additionally, composite resins have been bonded to the teeth for the purpose of correcting the bite of a patient. The composite resin may be applied to the upper surface of several teeth simultaneously and the mouth then closed in the desired therapeutic jaw position to establish the proper bite. With this approach, it is difficult to prevent the composite resin from ending up in the interproximal space between the teeth and it is also difficult to remove this resin from this space once it is there. If conventional interproximal strips are used between the teeth, they push adjacent teeth apart and thereby slightly change the positions of the teeth. When these strips are removed following the resin bonding treatment, the teeth return to their original positions, which makes the bite no longer as accurate as desired.

Therefore, Summer describes a matrix band (tooth spacer) in his U.S. Pat. No. 5,505,618. The tooth spacer is inserted between interproximal surfaces of a tooth to be treated, and an adjacent tooth. The tooth spacer comprises an elongated body having a pair of opposite transversely spaced sidewalls or edges, and a gingival edge and an occlusal edge (the term "gingival edge" refers to the edge of the body positioned closest to the patient's gum when the spacer is inserted in place). The elongated body has a recessed or thin central portion at least partially surrounded or enclosed by a peripheral portion. Also, the spacer may be bent to conform to the tooth shape during insertion. The spacer also includes the thin central portion and the thick portion.

The thin central portion is of a material that is sufficiently rigid to withstand being forced down between the adjacent teeth at a contact area. The thin central portion extends from the gingival edge to a location adjacent the occlusal edge. The thinned central portion is dimensioned to be larger than the contact area, and the central portion is extended all the way to the occlusal edge. However, it is preferred to have a thicker reinforcing portion of the tooth spacer bounding the central portion. The thin central portion is made by either a grinding, molding, casting, chemical etching, stamping or any other process suitable for achieving a recessed or thinned area. The height or distance the central portion extends from the gingival edge is from seventy-five to ninety-five percent of the overall height of the tooth spacer. The peripheral portion has a thickness greater than the thickness of the central portion to provide reinforcement and rigidity to the tooth spacer. Also, the peripheral portion extends between the central portion and the respective side walls and between the central portion and the occlusal edge. A reinforcing portion may is positioned along the gingival edge of the tooth spacer as this edge ends up in the gap below the contacting areas of the teeth after the tooth spacer has been inserted.

This spacer does not provide the sufficient contact of the spacer (matrix band) to the lower portion of the teeth (the distance between teeth at their lower portion is significantly bigger than the distance between teeth at their upper portion), and the spacer's position is not secure, that can cause an inadvertent displacement of the spacer during the dental procedure. Additionally, the known spacer is complex considering its multi-thickness, and the sharp lowest edge can injure the gingiva (if spacer stays not exactly vertically /under the angle to the horizontal level/ or gum (if spacer stays exactly vertically to the horizontal level).

Thus, there is a great need in the art for the improved not complex, not expensive and non-obstructive matrix band that is easily formed, placed, and removed, and that provides the convenience during dental procedure.

OBJECT AND ADVANTAGES OF THE INVENTION

Accordingly, several objects and advantages of the present invention are to provide convenient, effective not complex and not expensive dental tooth spacer assembly.

It is another object of the invention to minimize the amount of time required for placing, fixing and removing the tooth spacer in/off the patient mouth.

It is still another object of the invention to provide convenient tooth spacer for achieving dental restorations of the Class 2, Class 3 or Class 4 types.

It is yet another object of the invention to sufficiently protect (separate) the adjacent tooth during dental procedure on the restoring tooth.

It is further object of the invention to provide possibility of three-surface Class 2 restorations.

It is still further another object of the invention to prevent possible gingiva or gum injury by the sharp lower edge of the known spacers.

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

Most known dental tooth spacers, matrix bands are complex, have sharp edges dangerous for gum and/or gingiva.

Thus, there is a great need in the art for the improved not complex and not expensive dental tooth spacers (matrix bands).

An improved dental tooth spacer assembly provides higher convenience to operate with, and higher protection of the gingiva and/or gum from possible injury.

An improved dental tooth spacer assembly includes a separating portion made of a durable flexible material. The separating portion may comprise a first wall slightly higher than the height of the restoring tooth and a second wall including the bended portion overlapping the adjacent tooth. Also the improved dental tooth spacer assembly includes a fixing member comprising an elongated body, a first wing and a second wing.

DESCRIPTION OF THE PREFERRED EMBODIMENTS

Herein the description of an improved dental tooth spacer assembly will be done in statics (as if the components of the improved device are suspended in the space) with the description of their relative coupling to each other. The description of the functional operations of the improved dental tooth spacer assembly will be done hereinafter.

Figure 1A:
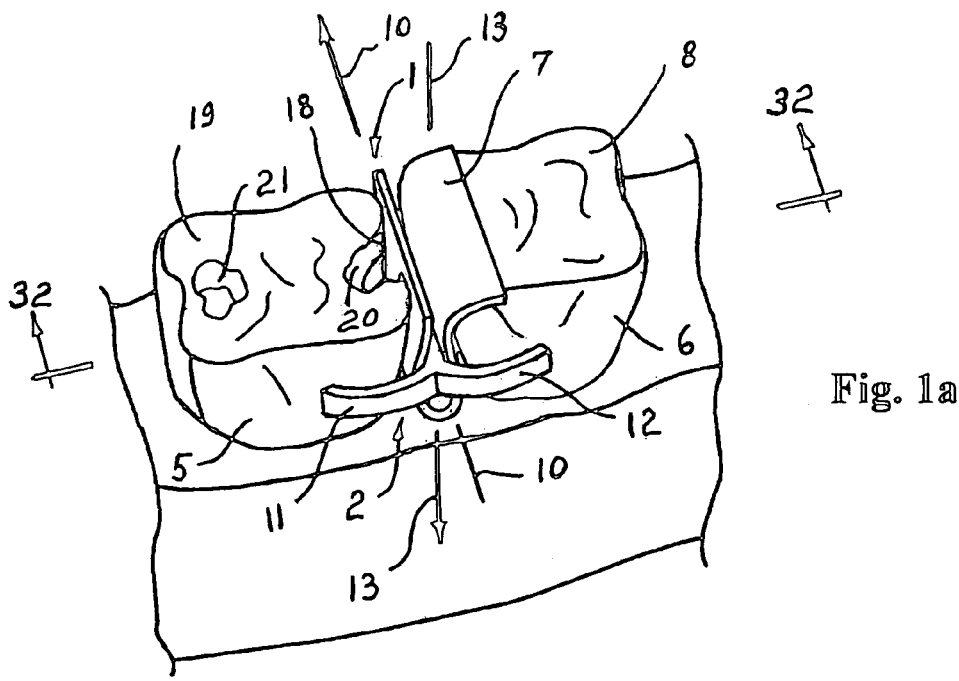
FIGS. 1a, 1b are the simplified spatial view of the improved dental tooth spacer assembly installation.
Figure 2A:
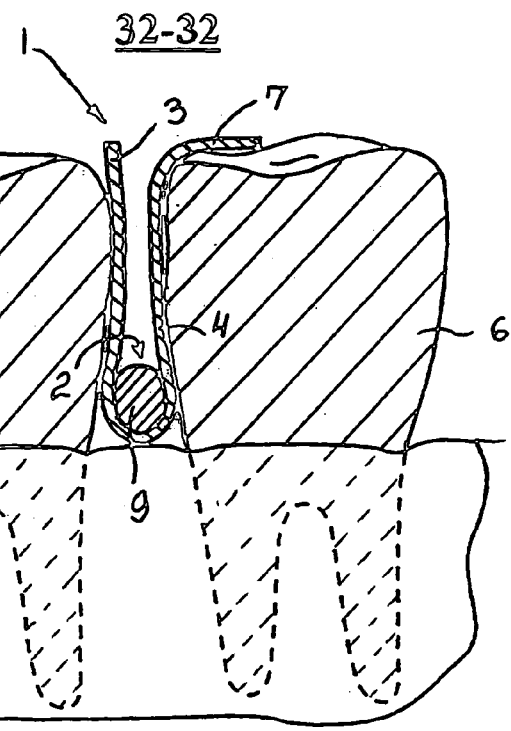
FIG. 2a is a cross-sectional view 32—32 of the improved dental tooth spacer assembly.
Figure 3A:
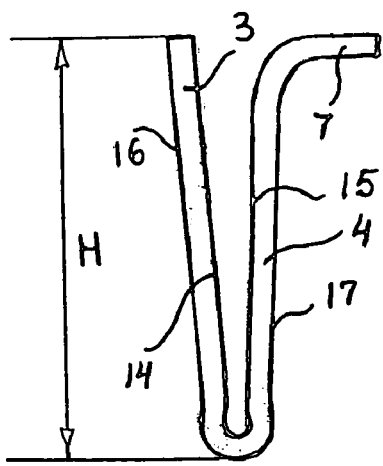
FIGS. 3a–3d are the simplified drawing of the separating portion.
Figure 3B:
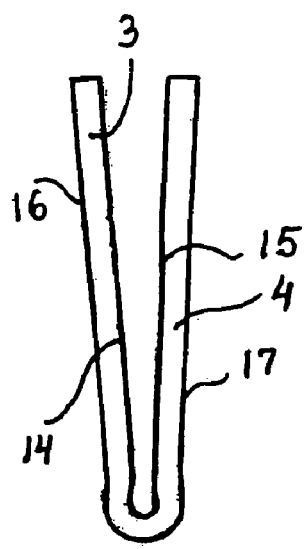
Figure 3C:
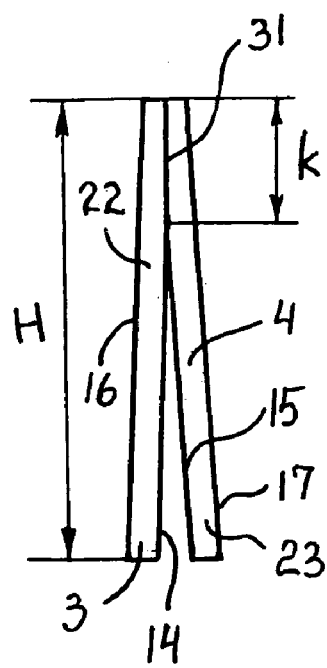

An improved dental tooth spacer assembly, referring to FIG. 1a, includes a separating portion 1, having a V-shape configuration, and a fixing member 2. The separating portion 1 comprises a first wall 3 and a second wall 4. As it is shown in FIGS. 1a, 2a, the separating portion 1 is installed between the restoring tooth 5 and adjacent tooth 6 in the direction of the longitudinal axis 13. According to the side view of the separating portion 1 shown in FIG. 3a, the first wall 3 has a height "H", which, for example, is slightly longer than the height "h" (see FIG. 2a) of the restoring tooth 5 (i.e. H>h), if needed when the first restoring area 21 is located, for instance, in the middle of the restoring tooth 5 horizontal surface 19. The height "H" of the first wall 3 can be slightly shorter than the height "h" of the restoring tooth 5 (H<h), if the second curing (restoring) area 20 is located at the edge of the horizontal surface 19 of the restoring tooth 5 closer to the spacer. The correlation of the heights "H" and "h" can have variety of ranges depending on the dental procedure necessity, for example, they can have the same height (H=h), etc. The second wall 4 includes the bended portion 7 which overlaps the upper (horizontal) surface 8 of the adjacent tooth 6. The bended portion 7 can slightly rounding the adjacent tooth 6 (not shown), or the second wall 4 can be configured identically to the first wall 3 (e.g. can be straight without bended portion 7, as shown in FIG. 3b). The separating portion 1 can be made of the solid sheet of the flexible, reliable, impervious to fluids in a person's mouth (e.g. such as water, saliva, etc.), non-reactive with dental chemicals, medications, fluid (e.g. such as water, saliva, etc.), and non-toxic material, preferably of the monolithic metallic material, e.g. such as a stainless steel or durable polymer material, etc. Also, the separating portion 1 can be made of two members: first separating member 22 and second separating member 23, as it is shown in FIGS. 3c, 3d, and will be described hereinfurther.

Figure 2B:
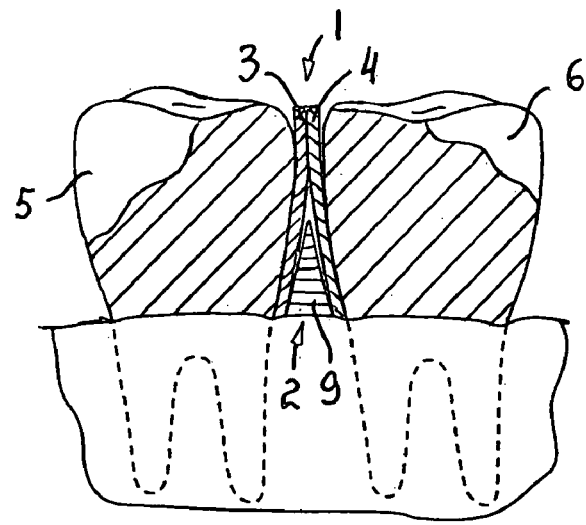
FIG. 2b is a simplified drawing of the another variant of the improved dental tooth spacer assembly.
Figure 4:
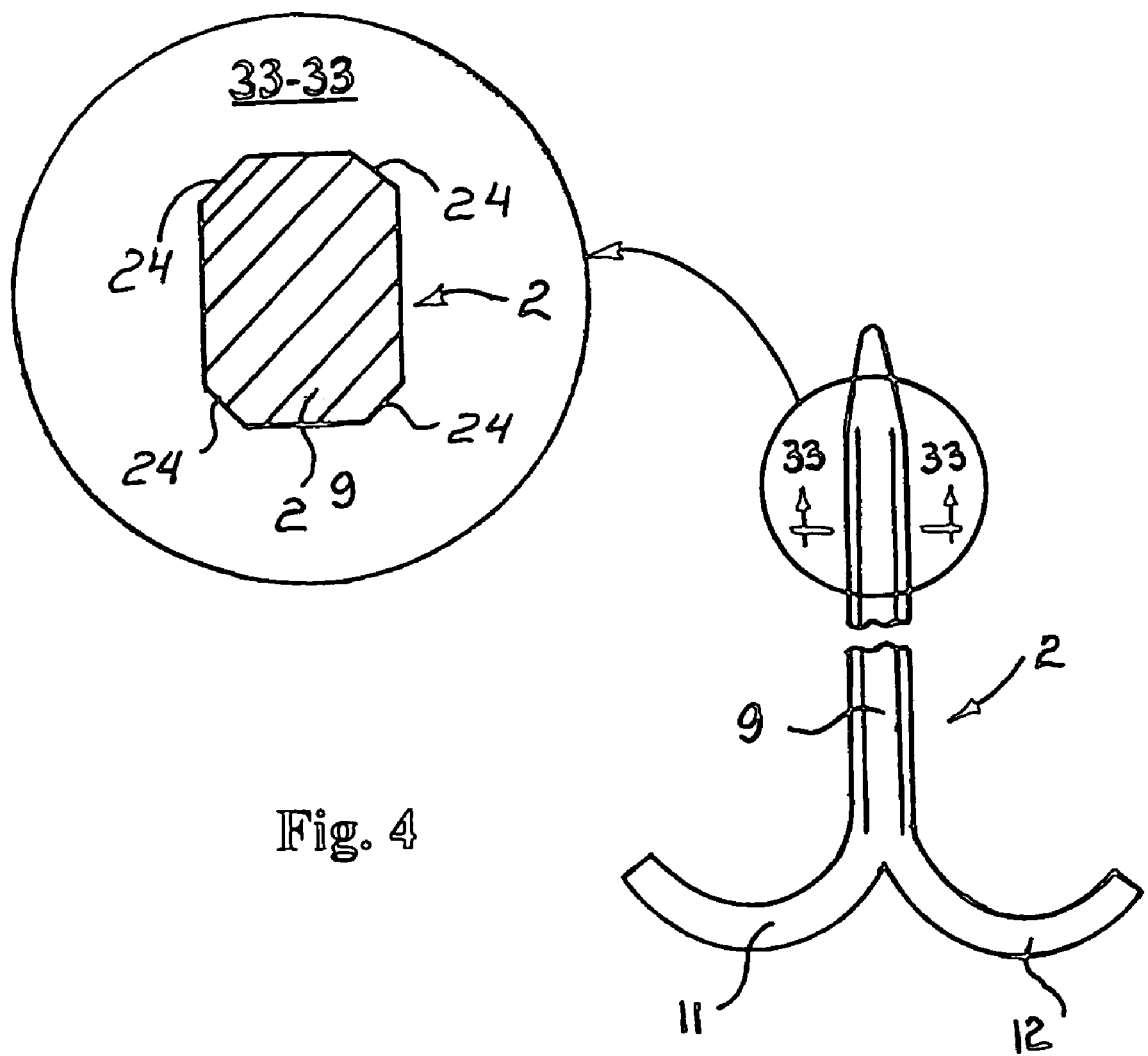
FIG. 4 is a simplified drawing of the fixing member top view.

Referring to FIG. 4, the fixing member 2 includes the body 9 elongated along the lateral axis 10 (see FIG. 1a), and the first 11 and second 12 wings respectively. The body 9, for instance, can preferably have the oval/elliptical configuration of its cross-section (see FIG. 2a), or be of rectangular form with not sharp angles 24, as shown in FIG. 4, or triangular (see FIG. 2b), circular (not shown) forms, etc. The fixing member 9 can be of any reasonable form, geometric configuration, e.g. such as of regular conic (not shown) or irregular conic form (not shown), etc. Each of the wings 11 and 12 is a semi-circular form and is rounding the appropriate tooth (e.g. restoring tooth 5 and adjacent tooth 6 respectively) in the manner shown in FIG. 1a. The fixing member 9 can be made also of the any slightly flexible and laterally compressible, reliable, impervious to fluids in a person's mouth (e.g. such as water, saliva, etc.), non-reactive with dental chemicals, medications, fluid (e.g. such as water, saliva, etc.), and non-toxic material, preferably of the monolithic durable polymer material, etc., but not necessarily, made of a metallic material, e.g. such as stainless steel.

The dental spacer assembly is installed between the teeth as following. The slightly compressed by the fingers separating portion 1 is installed between assigned teeth (e.g. between restoring tooth 5 and adjacent tooth 6, as shown in FIG. 1a. Then the fixing member 2 is inserted (either way from front side or rear/back side of the jaw) between inner surface 14 of the first wall 3 and inner surface 15 of the second wall 4 of the separating portion 1, thereby expending the space between first 3 and second 4 walls. That is provided by the space between teeth at the teeth lower area, where the distance between teeth at their lower portion is significantly bigger than the distance between teeth at their upper portion. The expansion of the walls 3 and 4 provides the two advantages: the first one is the fixing (securing displacement) of the separating portion 1 between the restoring tooth 5 and adjacent tooth 6, and the second one is the outer surface 16 of the first wall 3 is in more contact with the restoring tooth 5 and the outer surface 17 of the second wall 4 is in more contact with the adjacent tooth 6. The better coupling of the outer surface 16 of the spacer with the restoring tooth side surface 18 (see FIG. 1a) provides more effective protection gingiva from the possible contact with, for example, dental filling material.

Figure 1B:
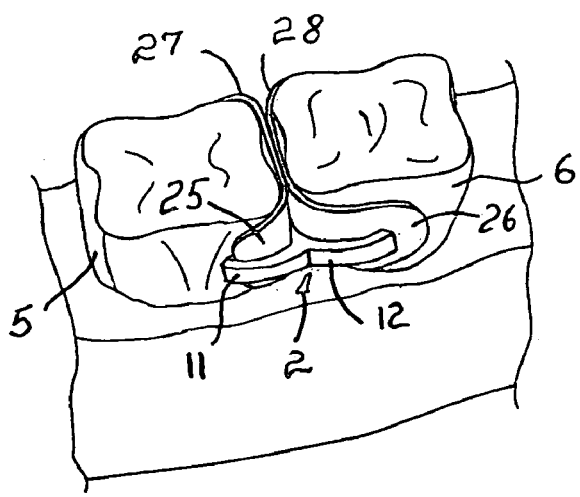
Figure 3D:
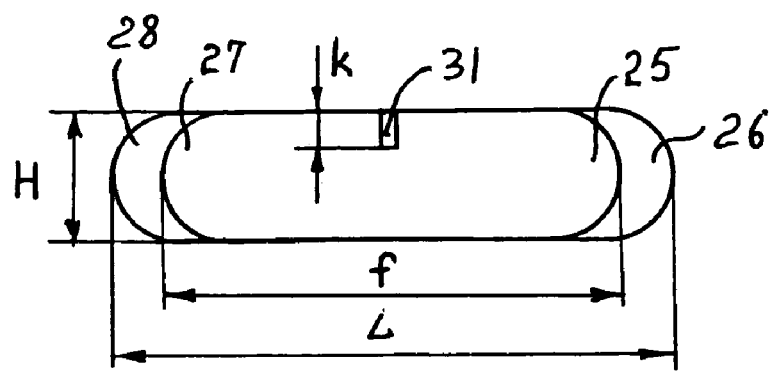

The first wall 3 and second wall 4 can include the first front wing 25, second front wing 26, first rear wing 27 and second rear wing 28, as shown in FIGS. 1b, 3d. The length "L" of the second separating member 23 can be slightly bigger than length "f" of the first separating member 22 (L>f) in order to provide easy installation of the fixing portion 2 (see FIG. 3d). The first 22 and second 23 separating members are rigidly connected to each other (e.g. by a direct electrical welding, etc.) in the connection area 31. The width "H" of the first 22 and second 23 separating members can be of any reasonable size (preferably, for instance, can be approximately from 5.0 mm to 15 mm), and the length "k" of the rigidly connected area (e.g. welded area) 31 can be of any needed dimensions (e.g. from 1 mm to 14 mm, etc.) considering the different client's teeth height. The separating members connecting area 31 can be located in any place along the longitudinal axis 13 positioned in the middle of the first 22 and second 23 separating members (the separating members connecting area 31 can be preferably located in the center /not shown/ of the first 22 and second 23 separating members). Such configuration of the separation portion 1 of the dental tooth spacer provides the best contact of the spacer with the equatorial areas of the restoring tooth 5 and adjacent tooth 6. Also, the simultaneous restoration of teeth 5 and 6 can be successfully provided by the dentist.

It should be understood that the above description discloses specific embodiments of the present invention and are for purposes of illustration only without any limitations. There may be other modifications and changes obvious to those of ordinary skill in the art which fall within the scope of the present invention.

CONCLUSION, RAMIFICATION AND SCOPE

Accordingly the reader will see that, according to the invention, I have provided the improved dental tooth spacer assembly. The improved dental tooth spacer assembly has various possibilities, considering activities and applications of the dental tooth spacers, matrix bands, etc providing separation (isolation) of the restoring tooth from the adjacent tooth.

While the above description contains many specificities, these should be not construed as limitations on the scope of the invention, but as exemplification of the presently-preferred embodiments thereof. Many other ramifications are possible within the teaching to the invention. For example, the improved dental tooth spacer assembly is reversible and can be easily reinstalled and effectively work for the adjacent tooth on left hand side or for the adjacent tooth on the right hand side of the restoring tooth, plus the bended portion of the second wall can be easily reshaped or be folded down, or can be eliminated (the second wall can be configured identically to the first wall /can be straight without bended portion/), etc.

Thus, the scope of the invention should be determined by the appended claims and their legal equivalents, and not by examples given.

---

THE DRAWING REFERENCE NUMERALS 1. a separating portion,
2. a fixing portion;
3. a first wall;
4. a second wall;
5. a restoring tooth;
6. an adjacent tooth;
7. a bended portion (of the second wall 4);
8. an upper surface of the adjacent tooth 6;
9. a body;
10. a lateral axis;
11. a first wing;
12. a second wing;
13. a longitudinal axis;
14. an inner surface of the first wall 3;
15. an inner surface of the second wall 4;
16. an outer surface of the first wall 3;
17. an outer surface of the second wall 4;
18. a restoring tooth side surface;
19. a horizontal surface of the restoring tooth 5;
20. a second restoring area of the tooth 5;
21. a first restoring area of the tooth 5;
22. a first separating member;
23. a second separating member;
24. rectangular's angle;
25. a first front wing;
26. a second front wing;
27. a first rear wing;
28. a second rear wing;
29. free;
30. free;
31. a connection area;
32–32 is a cross-sectional view;
33–33 is a cross-sectional view.

---

18.—a restoring tooth side surface;
19.—a horizontal surface of the restoring tooth 5;
20.—a second restoring area of the tooth 5;
21.—a first restoring area of the tooth 5;
22.—a first separating member;
23.—a second separating member;
24.—rectangular's angle;
25.—a first front wing;
26.—a second front wing;
27.—a first rear wing;
28.—a second rear wing;
29.—free;
30.—free;
31.—a connection area;
32—32 is a cross-sectional view;
33—33 is a cross-sectional view.

What is claimed is:

1. An improved dental tooth spacer assembly comprising
   a separating portion of V-shaped configuration for insertion between a restoring tooth and an adjacent tooth, and wherein said separating portion includes
      a first wall, having a height slightly longer than a height of said restoring tooth;
      a second wall, having a bended portion for overlapping a portion of a horizontal surface of said adjacent tooth;
   a fixing member of said dental tooth spacer assembly including
      an elongated body for insertion by one end of said elongated body between an inner surface of said first wall and an inner surface of said second wall along a lateral axis;
      a first wing extended from another end of said elongated body, and wherein said first wing is of a semi-circular form;
      a second wing extended from said another end of said elongated body, and wherein said second wing is of said semi-circular form, and wherein said first wing for rounding said restoring tooth and said second wing is for rounding said adjacent tooth.

2. An improved dental tooth spacer assembly comprising
   a separating portion for insertion between a restoring tooth and an adjacent tooth, and wherein said separating portion includes
      a first separating member comprising a first wall including a first front wing and a first rear wing;
      a second separating member comprising a second wall including a second front wing and a second rear wing, wherein said second separating member is slightly longer than said first separating member, and wherein said first separating member is rigidly connected to said second separating member in a connection area located in the middle of said first and second separating members along a longitudinal axis;
   a fixing member of said dental tooth spacer assembly for insertion between said first separating member and said second separating member, and including
      an elongated body for insertion by one end of said elongated body between an inner surface of said first wall and an inner surface of said second wall along a lateral axis;
      a first wing extended from another end of said elongated body, and wherein said first wing is of a semicircular form;
      a second wing extended from said another end of said elongated body, and wherein said second wing is of said semi-circular form, and wherein said first wing is for rounding said restoring tooth and said second wing is for rounding said adjacent tooth.

3. The tooth spacer of claim 2, wherein said elongated body is further of a triangularly-shaped cross-sectional configuration.

* * * * *